United States Patent [19]

Curran et al.

[11] 4,036,849
[45] July 19, 1977

[54] 1-(PARA-SUBSTITUTED-PHENYL)-1H-TETRAZOLES

[75] Inventors: William Vincent Curran, Pearl River, N.Y.; Andrew Stephen Tomcufcik, Old Tappan, N.J.; Adma Schneller Ross, Suffern, N.Y.

[73] Assignee: American Cyanamid Company, Stamford, Conn.

[21] Appl. No.: 630,562

[22] Filed: Nov. 10, 1975

Related U.S. Application Data

[63] Continuation-in-part of Ser. No. 470,083, May 15, 1974, abandoned.

[51] Int. Cl.$^2$ ............................................. C07D 257/04
[52] U.S. Cl. ................................. 260/308 D; 424/269
[58] Field of Search .................................. 260/308 D

[56] References Cited

U.S. PATENT DOCUMENTS

| 3,767,667 | 10/1973 | Kamiya et al. | 260/308 |
| 3,830,928 | 8/1974 | Mrozik | 260/308 |

FOREIGN PATENT DOCUMENTS

| 1,364,917 | 8/1974 | United Kingdom | 260/308 D |

OTHER PUBLICATIONS

*Chemical Abstracts,* vol. 43, 1864–1865 (1949).

*Primary Examiner*—Frederick E. Waddell
*Attorney, Agent, or Firm*—Edward A. Conroy, Jr.

[57] ABSTRACT

This disclosure describes compounds of the class of 1-(para-substituted-phenyl)-1H-tetrazoles useful as antimicrobial agents.

8 Claims, No Drawings

1-(PARA-SUBSTITUTED-PHENYL)-1H-TETRAZOLES

CROSS REFERENCE TO RELATED APPLICATION

This application is a continuation-in-part of our co-pending application Ser. No. 470,083, filed May 15, 1974, now abandoned.

BRIEF SUMMARY OF THE INVENTION

This invention relates to new organic compounds and, more particularly, is concerned with novel 1-phenyl-1H-tetrazoles substituted in the para-position of the phenyl moiety with various sulfur-containing functional groups. The novel compounds of the present invention may be represented by the following general formula:

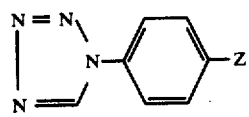

wherein Z is mercapto, methylthio, methylsulfinyl, methylsulfonyl, chloromethylthio, chloromethylsulfinyl, chloromethylsulfonyl, 4-pyridylthio, para-(1H-tetrazol-1-yl)phenyldithio, or moieties of the formulae:

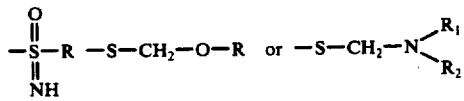

wherein R is lower alkyl, $R_1$ is lower alkyl, $R_2$ is lower alkyl, and $R_1$ and $R_2$ taken together with the associated N(itrogen) is morpholino, thiomorpholino, piperidino, pyrrolidino, or N-methylpiperazino. Suitable lower alkyl groups contemplated by the present invention are those having up to four carbon atoms such as methyl, ethyl, isopropyl, sec-butyl, etc. This invention is also concerned with novel methods of preparing these compounds.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, dimethylformamide, acetone, chloroform, ethyl acetate and the like. They are appreciably soluble in non-polar organic solvents such as diethyl ether, benzene, toluene, and the like but are relatively insoluble in water.

Certain of the novel compounds of the present invention may be readily prepared as illustrated by the following reaction schemes:

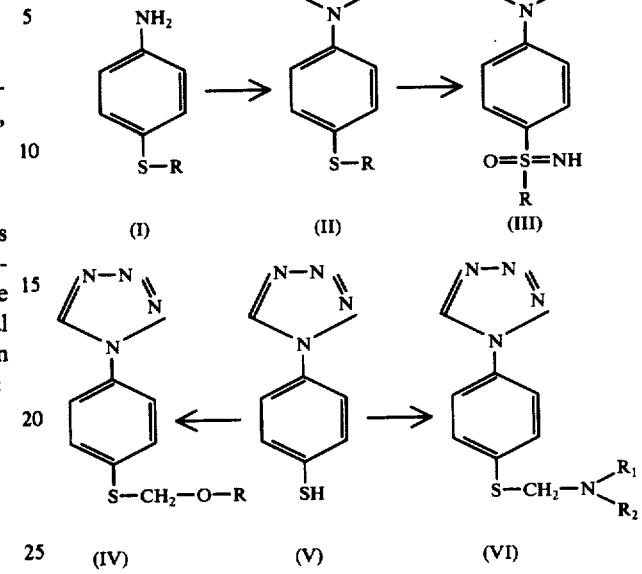

wherein R, $R_1$, and $R_2$ are as hereinabove defined. In accordance with the above reaction schemes, an appropriate p-(lower alkylthio)aniline (I) is first treated with an excess of triethylorthoformate in the presence of a mineral acid catalyst at the reflux temperature. This reaction mixture is then taken to dryness in vacuo and the residual oil is treated with sodium azide in glacial acetic acid solvent at room temperature whereby the 1-(p-lower alkylthiophenyl)-1H-tetrazole (II) is obtained. Further treatment of (II) with sodium azide in concentrated sulfuric acid at 35°-45° C. provides the corresponding S-lower alkyl-S-p-(1H-tetrazol-1-yl)phenylsulfoximine (III). Treatment of p-(1H-tetrazol-1-yl)benzenethiol (V) with formaldehyde and hydrogen bromide in an inert solvent at room temperature provides a crystalline intermediate which upon treatment with an appropriate lower alkanol at the reflux temperature provides the corresponding 1-[p-(lower alkoxymethylthio)phenyl]-1H-tetrazole (IV). Treatment of p-1H-tetrazol-1-yl)benzenethiol (V) with formalin and an appropriate secondary amine of the formula

at 0°-5° C. provides the corresponding 1-[p-(secondary aminomethylthio)phenyl[-1H-tetrazole (VI).

The novel compounds of the present invention are useful as antimicrobial agents and possess broad spectrum activity in vivo against Gram-negative and Gram-positive bacteria. The in vivo antibacterial activity of the novel compounds of the present invention makes them useful as additives to materials which are subject to microbial deterioration such as cutting oils and full oils. They are also useful in soaps, shampoos, and topical compositions for the treatment of wounds and burns.

The invention will be described in greater detail in conjunction with the following specific examples.

EXAMPLE 1

Preparation of p-(1H-tetrazol-1-yl)benzenethiol (A)

1,1'(Dithiodi-p-phenylene)-bis-1H-tetrazole (4.3 g.), zinc dust (4.0 g.), and acetic acid (100 ml.) were mixed and heated at reflux for 2 hours with stirring. On cooling, the mixture was filtered and the resulting solid extracted with 2.5N sodium hydroxide solution (100 ml.). This solution was acidified (concentrated hydrochloric acid) to give crystals, m.p. 120°–122° C.

Alternatively a mixture of p-aminothiophenol (9.0 g.), sodium azide (7.0 g.), triethyl orthoformate (30 ml.), and acetic acid (30 ml.) was stirred and heated at 85° C. for 30 minutes. The reaction mixture was evaporated at reduced pressure and diluted with water to give a crystalline product which was collected and recrystallized from chloroform:hexane.

EXAMPLE 2

Preparation of 1-(p-methylthiophenyl)-1H-tetrazole (B)

A mixture consisting of 21 grams of p-methylthioaniline, 150 ml. of triethylorthoformate, and 5 drops of concentrated sulfuric acid is stirred and gently refluxed under an air condenser so adjusted that the ethanol formed during the reaction is continually distilled out. When the evolution of ethanol ceases, the temperature is raised until the distillation of triethylorthoformate commences. The reaction mixture is cooled, 1 gram of sodium acetate added, and the mixture is then taken to dryness in vacuo. The residual oil is dissolved in 350 ml. of glacial acetic acid, 30 grams of powdered sodium azide added and the mixture stirred at room temperature for 12 to 24 hours. It is then drowned into 8 volumes of cold water, and the crude 1-(p-methylthiophenyl)-1H-tetrazole collected, washed with water, and dried. Recrystallization from 250 ml. of ethanol yields 16.6 g. of the pure compound melting at 126°–127° C.

EXAMPLE 3

Preparation of 1-[p-(methylsulfinyl)phenyl]-1H-tetrazole (C)

1-[p-(Methylthio)phenyl]-1H-tetrazole (2 g.) and 0.9 ml. of 30% hydrogen peroxide were refluxed with stirring in benzene for 3 hours. The benzene was decanted and the precipitate washed with benzene and recrystallized from acetone, m.p. 175°–176° C.

EXAMPLE 4

Preparation of 1-[p-(methylsulfonyl)phenyl]-1H-tetrazole (D)

The preparation of the subject compound is effected essentially by the procedure of Example 2, an equivalent of p-methylsulfonylaniline replacing the p-methylthioaniline. After recrystallization from a mixture of ethanol and dimethylformamide, the compound melts at 182°–183° C. with decomposition.

Alternatively, the subject compound is prepared by the oxidation of 1-(p-methylthiophenyl)-1-H-tetrazole (Example 2) with an excess of 30% aqueous hydrogen peroxide in glacial acetic acid solution at steam-bath temperature for four hours. Concentration of the solution to dryness in vacuo, followed by recrystallization of the residue from ethanol-dimethylformamide gives the product, identical to that produced by the former procedure.

EXAMPLE 5

Preparation of 1,1'-(dithiodi-p-phenylene)-bis-1H-tetrazole (E)

The preparation of the subject compound is carried out essentially by the procedure of Example 2, a one-half equivalent of 4,4'-diaminodiphenyl-1,1'-disulfide replacing the p-methylthioaniline. After recrystallization from ethanol-dimethylformamide, the compound melts at 207°–208° C. with decomposition.

The same product is obtained when one equivalent of p-aminothiophenol replaces the p-methylthioaniline. The 1-(p-mercaptophenyl)-1H-tetrazole formed initially is oxidized under the experimental conditions to the product identical to that obtained by the former procedure.

EXAMPLE 6

Preparation of 1-[p-(chlormethylthio)phenyl]-1H-tetrazole (F)

A solution of 4.8 g. of 1-[p-(methylthio)phenyl]-1H-tetrazole in 80 ml. of methylene chloride was treated with 2.2 ml. of sulfuryl chloride in 10 ml. of methylene chloride. The solution was stirred at room temperature for 1 hour, evaporated to dryness on a steam bath, washed with hexane and recrystallized from methylene chloride to give white crystals, m.p. 115°–117° C. This product was also obtained by a similar reaction of 0.5 g. of 1-[p-(methylsulfinyl)phenyl]-1H-tetrazole and 0.18 ml. of thionyl chloride in methylene chloride.

EXAMPLE 7

Preparation of 1-[p-(chloromethylsulfinyl)phenyl-1-H-tetrazole (G)

To a stirred suspension of 0.5 g. of 1-[p-methylsulfinyl)phenyl[-1H-tetrazole in 20 ml. of methylene chloride was added dropwise a solution of 0.22 ml. of sulfuryl chloride in 5 ml. of methylene chloride. After 30 minutes at room temperature and one hour at reflux, crystals were filtered off. Recrystallization from methylene chloride-hexane gave white crystals, m.p. 147°–149° C.

EXAMPLE 8

Preparation of 1-[p-(chloromethylsulfonyl)phenyl]tetrazole (H)

A solution of 226 mg. of 1-[p-(chloromethylthio)-phenyl]-1H-tetrazole and 0.35 ml. of 30% hydrogen peroxide in 2 ml. of glacial acetic acid was refluxed 15 minutes, cooled, and diluted with water. Crystals filtered off and recrystallized from ethanol gave m.p. 168°–171.5° C.

EXAMPLE 9

Preparation of 4-[p-(1H-tetrazol-1-yl)phenylthio])pyridine (I)

A mixture of 1.08 g. of sodium methoxide, 1.78 g. of p-1H-tetrazol-1-ylbenzenethiol, and 1.94 g. of 4-bromopyridine hydrochloride in 20 ml. of ethanol was refluxed 4½ hours. Ethanol was evaporated and the residue was washed with water and recrystallized from acetone-hexane to give white crystals, m.p. 127°–128.5° C.

EXAMPLE 10

Preparation of
1-[p-(dimethylaminomethylthio)phenyl]-1H-tetrazole
(J)

To 1.0 ml. (10 mmol) of formalin at 0°-5° C. was added dropwise, with stirring, 1.1 ml. (10 mmol) of dimethylamine. After 20 minutes stirring, 1.78 g. (10 mmol) of p-(1H-tetrazol-1-yl)benzenethiol was added all at once followed by solid sodium carbonate. The mixture was stoppered, stirred vigorously for 1½ hours, and dichloromethane added. The dichloromethane layer was washed with water, dried, and evaporated to give white crystals, m.p. 56°-57.5° C.

EXAMPLE 11

Preparation of
1-[p-(diethylaminomethylthio)phenyl]-1H-tetrazole (K)

The procedure of Example 10 is repeated substituting an equimolecular amount of diethylamine for the dimethylamine employed in that example. There is thus obtained the 1-[p-(diethylaminomethylthio)phenyl]-1H-tetrazole in equally good yield.

EXAMPLE 12

Preparation of
4-(1H-tetrazole-1-yl)phenylthiomethyl]morpholino (L)

Following the general procedure of Example 10, p-(1H-tetrazol-1-yl)benzenethiol is treated with formalin and morpholine to give the 4-[p-(1H-tetrazol-1-yl)phenylthiomethyl]morpholine as white crystals from dichloromethane-hexane, m.p. 118.5°-121° C.

By replacing the morpholine in this example with an equimolar amount of thiomorpholine, piperidine, pyrrolidine, or N-methylpiperazine there is obtained the corresponding 4-[p-1H-tetrazol-1-yl)phenylthiomethyl]thiomorpholine (M), 1-[p-(1H-tetrazol-1-yl)phenylthiomethyl]piperidine (N), 1-[p-(1H-tetrazol-1-yl)phenylthiomethyl]pyrrolidine (O), and 1-methyl-4-[p-(1H-tetrazol-1-yl)phenylthiomethyl]piperazine (P).

EXAMPLE 13

Preparation of
1-[p-(ethoxymethylthio)phenyl]-1H-tetrazole (Q)

Hydrogen bromide was bubbled into a suspension of 0.89 g. of p-1H-tetrazol-1-ylbenzenethiol in 200 ml. of benzene. Paraformaldehyde (0.16 g.) was added slowly and the mixture stirred at room temperature. Crystals were filtered off and refluxed 20 minutes in ethanol. Upon cooling, white crystals, m.p. 95°-98° C., were obtained.

EXAMPLE 14

Preparation of
1-[p-(isopropoxymethylthio)phenyl]-1H-tetrazole (R)

The general procedure of Example 13 is repeated but replacing the ethanol employed in that example with isopropanol whereby there is obtained the 1-[p-(isopropoxymethylthio)phenyl]-1H-tetrazole.

EXAMPLE 15

Preparation of
S-methyl-S-[p-(1H-tetrazol-1-yl)phenyl]sulfoximine (S)

Sodium azide (2.6 g.) was added at 35°-45° C. over 1½ hours to a stirred mixture of 1.78 g. (0.01 mol) of 1-[p-(methylthio)phenyl]-1H-tetrazole and 6 ml. of concentrated sulfuric acid. After 4 additional hours of stirring the chloroform was poured off, the remaining paste diluted with water, filtered, and the filtrate adjusted to pH 8.5 and chilled. White crystals, m.p. 180°-181° C. were isolated.

EXAMPLE 16

Preparation of
S-ethyl-S-[p-(1H-tetrazol-1-yl)phenyl]sulfoximine (T)

Following the general procedure of Example 15, 1-[p-(ethylthio)phenyl]-1H-tetrazole (prepared from p-ethylthioaniline by the method of Example 2) is treated with sodium azide and concentrated sulfuric acid to give the S-ethyl-S-[p-(1H-tetrazole-1-yl)-phenyl]sulfoximine.

EXAMPLE 17

In vivo activity of the
1-(para-substituted-phenyl)-1H-tetrazoles

The novel compounds of the present invention are active in vivo against a variety of microorganisms. These new antimicrobial agents are thereby potentially useful as therapeutic agents in treating bacterial infections in mammals. The usefulness of these new antimicrobial agents was shown by their ability to control systemic lethal infections in mice in the following test procedure.

The animals used were Carworth Farms CF-1 strain female mice approximately 6 weeks old and averaging 18-22 gm. in weight. Infections were produced by intraperitoneal injections of a 0.5 ml. volume (a lethal dose) of a trypticase soy broth (TSP) dilution (as indicated in Table I) of a 5 hour TSP blood culture of the microorganisms listed in Table I below.

TABLE I

| Microorganism | TSP dilution of a 5 hour TSP culture |
|---|---|
| Proteus mirabilis ATCC 46/1 | 1:40 |
| Escherichia coli 311 | 10−3 |
| Klebsiella pneumoniae AD | 10−4 |
| Pseudomonas aeruginosa PA7 | 10−3 |
| Salmonella typhosa ATCC 6539 | undiluted |
| Aerobacter aerogenes 75 | 10−1 |
| Streptococcus pyogenes C203 | 10−5 |
| Staphylococcus aureus ATCC 13709 | 10−2 |
| Staphylococcus aureus ATCC 14154 | 10−0.5 |
| Diplococcus pneuoniae SV1 | undiluted |

The test compounds were administered either in a single 0.5 ml. oral tubing dose or by a single 0.5 ml. subcutaneous dose in 0.2% aqueous agar immediately after infection at the indicated dosage levels. The results are set forth in Tables II-XIII, below, as percent effectiveness (alive/total) at 14 days post infection for each dosage level. The test compounds are identified in Tables II-XIII by the capital letter designation recited in the titles of the preparative examples.

TABLE II

| Oral Dose (mg./kg.) | Percent Effect (Alive/Total) with *Escherichia coli* 311 | | | | | |
|---|---|---|---|---|---|---|
| | (B) | (D) | (C) | (A) | (F) | (G) |
| 1024 | | | 100(10/10) | | | |
| 256 | 100(20/20) | 100(20/20) | 100(5/5) | | 20(1/5) | 100(5/5) |
| 128 | 83(25/30) | 90(27/30) | 60(6/10) | | 60(3/5) | 100(5/5) |
| 64 | 52(21/40) | 45(18/40) | 48(12/25) | | 0(0/5) | 60(3/5) |
| 32 | 17(5/30) | 30(9/30) | 5(1/20) | | 60(3/5) | 60(3/5) |
| 16 | 13(4/30) | 23(7/30) | 20(5/25) | | 0(0/5) | 40(2/5) |
| 8 | 0(0/20) | 10(2/20) | 10(2/20) | | 0(0/5) | 20(1/5) |
| 4 | 0(0/10) | 10(1/10) | 0(0/10) | | | |
| 2 | 0(0/10) | 0(0/10) | 0(0/10) | | | |
| Subcutaneous Dose (mg./kg.) | (B) | (D) | (C) | (A) | (F) | (G) |
| 1024 | | | | 0(0/5) | | |
| 512 | | | 100(5/5) | 0(0/5) | | |
| 256 | 95(19/20) | 100(5/5) | 100(15/15) | 0(0/5) | | |
| 128 | 95(19/20) | 80(12/15) | 80(16/20) | | | |
| 64 | 55(11/20) | 87(13/15) | 80(16/20) | | | |
| 32 | 30(3/10) | 40(4/10) | 30(6/20) | | | |
| 16 | 0(0/10) | 20(2/10) | 10(2/20) | | | |
| 8 | | 10(1/10) | 0(0/10) | | | |
| 4 | | | 0(0/10) | | | |
| Infected Non-treated Controls | 2(3/150) | | | | | |
| Normal Controls | 100(45/45) | | | | | |

TABLE III

| Oral Dose (mg./kg.) | Percent Effect (Alive/Total) with *Klebsiella pneumonia* AD | | | |
|---|---|---|---|---|
| | (B) | (D) | (C) | (A) |
| 1024 | 46(14/30) | 80(24/30) | 88(22/25) | 0(0/5) |
| 512 | 45(9/20) | 63(19/30) | 55(11/20) | |
| 256 | 20(4/20) | 47(14/30) | 25(5/20) | |
| 128 | 0(0/10) | 5(1/20) | 5(1/20) | |
| Subcutaneous Dose (mg./kg.) | (B) | (D) | (C) | (A) |
| 1024 | 10(2/20) | 90(18/20) | | |
| 512 | 5(1/20) | 65(13/20) | 20(3/15) | 0(0/5) |
| 256 | 5(1/20) | 25(5/20) | 27(4/15) | 0(0/5) |
| 128 | | 5(1/20) | 7(1/15) | 0(0/5) |
| Infected Non-Treated Controls | 0(0/50) | | | |
| Normal Controls | 100(10/10) | | | |

TABLE IV

| Oral Dose (mg./kg.) | Percent Effect (Alive/Total) with *Pseudomonas aeruginosa* PA7 | | |
|---|---|---|---|
| | (B) | (D) | (C) |
| 1024 | 0(0/5) | 0(0/5) | 20(1/5) |
| 512 | 20(1/5) | 0(0/5) | 0(0/5) |
| Infected Non-Treated Controls | 0(0/30) | | |
| Normal Controls | 100(5/5) | | |

TABLE V

| Oral Dose (mg./kg.) | Percent Effect (Alive/Total) with *Salmonella typhosa* ATCC 6539 | | | |
|---|---|---|---|---|
| | (B) | (D) | (C) | (A) |
| 1024 | 37(11/30) | 53(16/30) | 83(25/30) | 20(1/5) |
| 512 | 30(10/30) | 63(19/30) | 70(21/30) | |
| 256 | 50(10/20) | 75(15/20) | 50(10/20) | |
| 128 | 60(6/10) | 45(9/20) | 50(10/20) | |
| 64 | 40(4/10) | 30(6/20) | 40(8/20) | |
| 32 | | | 10(1/10) | |
| 16 | | | 10(1/10) | |
| Subcutaneous Dose (mg./kg.) | (B) | (D) | (C) | (A) |
| 1024 | 40(12/30) | 73(22/30) | | |
| 512 | 23(7/30) | 76(23/30) | 93(28/30) | 0(0/5) |
| 256 | 30(6/20) | 70(14/20) | 67(20/30) | |
| 128 | 30(3/10) | 45(9/20) | 75(15/20) | |
| 64 | | 25(5/20) | 35(7/20) | |
| 32 | | 50(5/10) | 40(4/10) | |
| 16 | | | 10(1/10) | |
| Infected Non-Treated Controls | 5(5/100) | | | |

TABLE VI

| Oral Dose (mg./kg.) | Percent Effect (Alive/Total) with *Aerobacter aerogenes* 75 | | | |
|---|---|---|---|---|
| | (B) | (D) | (C) | (A) |
| 1024 | 0(0/15) | 12(3/25) | 12(3/25) | 0(0/5) |
| 512 | 0(0/10) | 20(4/20) | 55(11/20) | |
| 256 | 0(0/10) | 10(2/20) | 20(4/20) | |
| 128 | | 5(1/20) | 0(0/20) | |
| Subcutaneous Dose (mg./kg.) | (B) | (D) | (C) | (A) |
| 1024 | 0(0/5) | 0(0/15) | | |
| 512 | | 0(0/10) | 13(2/15) | 0(0/5) |
| 256 | | 0(0/10) | 0(0/10) | |
| 128 | | 20(2/10) | 0(0/10) | |
| 64 | | | 10(1/10) | |
| Infected Non-Treated Controls | 1(1/100) | | | |
| Normal Controls | 100(10/10) | | | |

TABLE VII

| Oral Dose (mg./kg.) | Percent Effect (Alive/Total) with *Streptococcus pyogenes* C203 | | | |
|---|---|---|---|---|
| | (B) | (D) | (C) | (A) |
| 1024 | 47(7/15) | 40(6/15) | 47(7/15) | 60(3/5) |
| 512 | 0(0/10) | 20(2/10) | 30(3/10) | |
| Subcutaneous Dose (mg./kg.) | (B) | (D) | (C) | (A) |
| 1024 | 13(2/15) | 33(5/15) | 10(1/10) | |
| 512 | 0(0/10) | 0(0/10) | 0(0/15) | 0(0/5) |
| 256 | 10(1/10) | 0(0/10) | 10(1/10) | |
| Infected Non-Treated Controls | 0(0/50) | | | |

TABLE VIII

| Oral Dose (mg./kg.) | Percent Effect (Alive/Total) with *Staphylococcus aureus* ATCC 13709 | | | |
|---|---|---|---|---|
| | (B) | (D) | (C) | (A) |
| 1024 | 7(1/15) | 27(4/15) | 47(7/15) | 40(2/5) |
| 512 | 0(0/10) | 10(1/10) | 0(0/10) | |
| 256 | 10(1/10) | 10(1/10) | 0(0/10) | |
| Subcutaneous Dose (mg./kg.) | (B) | (D) | (C) | (A) |
| 1024 | 20(3/15) | 27(4/15) | | |
| 512 | 0(0/10) | 20(2/10) | 20(3/15) | 20(1/5) |
| 256 | 0(0/10) | 0(0/10) | 0(0/10) | |
| 128 | 0(0/10) | 0(0/10) | 10(1/10) | |
| 64 | | | 10(1/10) | |
| Infected Non-Treated Controls | 8(3/40) | | | |

TABLE IX

| | Percent Effect (Alive/Total) with Staphylococcus aureus ATCC 14154 | | |
|---|---|---|---|
| Oral Dose (mg./kg.) | (B) | (D) | (C) |
| 1024 | 0(0/5) | 0(0/5) | 0(0/5) |
| 512 | 0(0/5) | 20(1/5) | 20(1/5) |
| 256 | 20(1/5) | 0(0/5) | 20(1/5) |
| Subcutaneous Dose (mg./kg.) | (B) | (D) | (C) |
| 1024 | 0(0/5) | 0(0/5) | 40(2/5) |
| 512 | 20(1/5) | 20(1/5) | 0(0/5) |
| 256 | 0(0/5) | 0(0/5) | 0(0/5) |
| Infected Non-Treated Controls | 0(0/40) | | |

TABLE X

| | Percent Effect (Alive/Total with Proteus mirabilis ATCC 4671 | | | | | |
|---|---|---|---|---|---|---|
| Oral Dose (mg./kg.) | (B) | (D) | (C) | (A) | (F) | (G) |
| 1024 | 100(5/5) | | | | | |
| 512 | 100(5/5) | 100(10/10) | 100(5/5) | 100(5/5) | | |
| 256 | | 100(10/10) | 100(10/10) | 100(10/10) | | |
| 128 | 96(24/25) | 100(5/5) | 100(5/5) | 100(5/5) | | |
| 64 | | 84(21/25) | 88(22/25) | 100(5/5) | | |
| 32 | 44(11/25) | | | | | |
| 16 | | 36(9/25) | 40(10/25) | 100(5/5) | | |
| 8 | 16(4/25) | | | | | |
| 4 | | 32(8/25) | 20(5/25) | 60(3/5) | | |
| 2 | 5(1/20) | | | | | |
| 1 | | 5(1/20) | 15(3/20) | | | |
| 0.5 | 10(2/20) | | | | | |
| 0.25 | | 25(5/20) | 15(3/20) | | | |
| Subcutaneous Dose (mg./kg.) | (B) | (D) | (C) | (A) | (F) | (G) |
| 1024 | 53(8/15) | | | | | |
| 512 | 70(7/10) | | | | | |
| 256 | 80(8/10) | | | | | 100(5/5) |
| 128 | 85(17/20) | 95(19/20) | 90(18/20) | 25(5/20) | 40(2/5) | 80(4/5) |
| 64 | 30(6/20) | 70(14/20) | 95(19/20) | 55(11/20) | 0(0/5) | 20(1/5) |
| 32 | 50(5/10) | 50(10/20) | 60(12/20) | 70(14/20) | 40(2/5) | 0(0/5) |
| 16 | 20(2/10) | 35(7/20) | 35(7/20) | 45(9/20) | 0(0/5) | 0(0/5) |
| 8 | 10(1/10) | 10(1/10) | 25(5/20) | 50(5/10) | 0(0/5) | 0(0/5) |
| 4 | | | 30(3/10) | 0(0/10) | 0(0/5) | 0(0/5) |
| Infected Non-Treated Controls | 9(7/80) | | | | | |
| Normal Controls | 98(59/60) | | | | | |

TABLE XI

| | Percent Effect (Alive/Total) with Diplococcus pneumoniae SV1 | | |
|---|---|---|---|
| Oral Dose (mg./kg.) | (B) | (D) | (C) |
| 1024 | 20(3/15) | 13(2/15) | 20(3/15) |
| 256 | 0(0/15) | 0(0/15) | 0(0/15) |
| 64 | 0(0/15) | 0(0/15) | 0(0/15) |
| Subcutaneous Dose (mg./kg.) | (B) | (D) | (C) |
| 1024 | 53(8/15) | 27(4/15) | |
| 512 | 40(4/10) | 10(1/10) | 0(0/15) |
| 256 | 13(2/15) | 0(0/15) | 0(0/10) |
| 128 | 0(0/10) | 0(0/10) | 0(0/15) |
| 64 | 0(0/15) | 0(0/15) | 0(0/10) |
| 32 | 0(0/10) | 0(0/10) | 0(0/15) |
| Infected Non-Treated Controls | 0(0/40) | | |

| | Percent Effect (Alive/Total) with Escherichia coli 311 | | |
|---|---|---|---|
| Oral Dose (mg./kg.) | (E) | (H) | (I) |
| 128 | 50(1/2) | 0(0/2) | 0(0/2) |
| Oral Dose (mg./kg.) | (J) | (L) | (Q) | (S) |
| 128 | 50(1/2) | 0(0/2) | 0(0/2) | 0(0/2) |
| Infected Non-Treated Controls | 2(3/150) | | | |

TABLE XIII

| Subcutaneous Dose (mg./kg.) | Percent Effect (Alive/Total) with Proteus mirabilis (ATCC 4671) | | |
|---|---|---|---|
| | (E) | (H) | (I) |
| 256 | 100(5/5) | | 20(1/5) |
| 128 | 40(2/5) | 0(0/2) | 100(5/5) |
| 64 | 20(1/5) | | 40(2/5) |
| Subcutaneous Dose (mg./kg.) | (J) | (L) | (Q) | (S) |
| 256 | | 100(5/5) | 100(5/5) | 60(3/5) |
| 128 | 100(2/2) | 100(5/5) | 80(4/5) | 60(3/5) |
| 64 | | 80(4/5) | 100(5/5) | 60(3/5) |
| Infected Non-Treated Controls | 9(7/80) | | | |

We claim:

1. A compound of the formula:

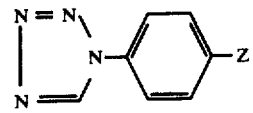

wherein Z is selected from the group consisting of moieties of the formulae:

—SH, —SCH$_2$X, —SOCH$_2$X and —SO$_2$CH$_2$X wherein X is selected from the group consisting of hydrogen and chlorine.

2. The compound according to claim 1 wherein Z is mercapto; p-(1H-tetrazol-1-yl)benzenethiol.

3. The compound according to claim 1 wherein Z is methylthio; 1-[p-(methylthio)phenyl]-1H-tetrazole.

4. The compound according to claim 1 wherein Z is methylsulfinyl; 1-[p-(methylsulfinyl)phenyl]-1H-tetrazole.

5. The compound according to claim 1 wherein Z is methylsulfonyl; 1-[p-(methylsulfonyl)phenyl]-1H-tetrazole.

6. The compound according to claim 1 wherein Z is chloromethylthio; 1-[p-(chloromethylthio)phenyl]-1H-tetrazole.

7. The compound according to claim 1 wherein Z is chloromethylsulfinyl; 1-[p-(chloromethylsulfinyl)phenyl]-1H-tetrazole.

8. The compound according to claim 1 wherein Z is chloromethylsulfonyl; 1-[p-(chloromethylsulfonyl)phenyl]-1H-tetrazole.

* * * * *